(12) United States Patent
Savica

(10) Patent No.: US 7,815,898 B2
(45) Date of Patent: Oct. 19, 2010

(54) ORAL COMPOSITIONS FOR ABSORPTION OF PHOSPHORUS COMPOUNDS

(75) Inventor: Vincenzo Savica, Messina (IT)

(73) Assignee: CM&D Pharma Limited, London (GB)

( * ) Notice: Subject to any disclaimer, the term of this patent is extended or adjusted under 35 U.S.C. 154(b) by 540 days.

(21) Appl. No.: 11/792,047

(22) PCT Filed: Nov. 29, 2005

(86) PCT No.: PCT/EP2005/056289

§ 371 (c)(1), (2), (4) Date: Jun. 1, 2007

(87) PCT Pub. No.: WO2006/061336

PCT Pub. Date: Jun. 15, 2006

(65) Prior Publication Data

US 2008/0125394 A1 May 29, 2008

(30) Foreign Application Priority Data

Dec. 7, 2004 (IT) .......................... ME2004A0015

(51) Int. Cl.
- *A61K 9/68* (2006.01)
- *A61K 31/765* (2006.01)
- *A61K 31/785* (2006.01)
- *A61K 31/74* (2006.01)
- *A61K 31/722* (2006.01)
- *A61K 33/06* (2006.01)
- *A61K 33/10* (2006.01)

(52) U.S. Cl. ...................... 424/48; 424/78.1; 424/78.11; 424/78.12; 424/686; 424/687; 424/600; 424/715

(58) Field of Classification Search ........................ None
See application file for complete search history.

(56) References Cited

U.S. PATENT DOCUMENTS

| 4,163,777 | A |   | 8/1979 | Mitra |
|---|---|---|---|---|
| 4,181,718 | A | * | 1/1980 | Mason et al. ................. 514/60 |
| 4,814,176 | A |   | 3/1989 | Makino et al. |
| 5,496,545 | A |   | 3/1996 | Holmes-Farley et al. |
| 5,968,976 | A |   | 10/1999 | Murrer et al. |
| 2003/0138518 | A1 |   | 7/2003 | Kiefer et al. |

FOREIGN PATENT DOCUMENTS

| EP | 0 426 098 B1 | | 5/1991 |
|---|---|---|---|
| EP | 0 793 960 B1 | | 9/1997 |
| EP | 1 046 410 A3 | | 10/2000 |
| JP | 62-132830 | | 6/1987 |
| JP | 05-213762 | | 8/1993 |
| WO | 02/051259 A1 | | 7/2002 |
| WO | 2005/018651 | | 3/2005 |
| WO | 2005/041902 | | 5/2005 |
| WO | WO2006/050314 | * | 5/2006 |

OTHER PUBLICATIONS

The Merck Index, Twelfth Edition, published 1996 by Merck Research Laboratories, pp. 270-278 and 968-971.*
Locateli et al., "The importance of early detection of chronic kidney disease" Nephrol. Dial. Transplant. (2002) vol. 17 suppl. 11, pp. 2-7.*
Tonelli et al., N. Engl. J. Med. (2010) vol. 362, pp. 1312-1324.*
Savica et al., J. Am. Soc. Nephrol. (2009) vol. 20 pp. 639-644.*
"Fosrenol (R) Approved to Reduce Phosphorus Levels in End-Stage Renal Disease Patients", Shire Pharmaceuticals Group PLC (2004); retrieved from http://www.newswise.com/articles/view/507957 (Online 2006).
Schiller et al., "Effect of the Time of Administration of Calcium Acetate on Phosphorus Binding", New England Journal of Medicine, vol. 320, pp. 1110-1113 (1989).
Smith et al., "Aluminum Hydroxide: Evaluation of Two Dosage Forms and Two Dosing Schedules in Reducing Intestinal Phosphate Absorption", American Journal of Hospital Pharmacy, vol. 35, pp. 58-61 (1978).
Salivary Phosphorous Binding: A Novel Approach to Control Hyperphosphatemia. (J. Am. Soc. Nephrol. 20:460-462, 2009).
Tonelli et al., N. Engl. J. Med. 2010;362:1312-24, 1313.
Savica et al., J. Am. Soc. Nephrol., 20:939-644, 2009.
McMillan, James L.; The Merck Manual; "Chronic Kidney Disease—Renal Failure"; Rev. Dec. 2007; 7 pages. http://www.merck.com/mmpe/sec17/ch233/ch233c.html.
"The Merck Index—An Encyclopedia Of Chemicals, Drugs and Biologicals"; Third Edition, Merck & Co., Inc.; 3 pages, (2001).
Salusky; "A New Era In Phosphate Binder Therapy: What Are The Options?"; Kidney International, 2006 (70) S10-S15; 6 pages.
FDA approved label for Renagel® (sevelamer) (Oct. 2007).
FDA approved label for Fosrenol® (lanthanum carbonate) (revised Oct. 2009).
Chewing Gum Helps Treat Hyperphosphatemia in Kidney Disease Patients (Feb. 2009).

* cited by examiner

*Primary Examiner*—Eric S Olson
(74) *Attorney, Agent, or Firm*—Blank Rome LLP

(57) ABSTRACT

The present invention provides medicaments useful for reducing phosphorus serum level, especially in those subjects affected from hyperphosphatemia. More specifically, the present invention relates to pharmaceutical compositions to be administered by oral route in fasting periods, in order to absorb phosphorus compounds from fluids of the enteric tract, especially from saliva.

11 Claims, No Drawings

ORAL COMPOSITIONS FOR ABSORPTION OF PHOSPHORUS COMPOUNDS

This application is the U.S. national phase of International Application No. PCT/EP2005/056289 filed 29 Nov. 2005 which designated the U.S. and claims priority to IT ME2004A000015 filed 7 Dec. 2004, the entire contents of each of which are hereby incorporated by reference.

The present invention relates to the medical, in particular the pharmaceutical field, and deals with the problem of reducing phosphorus serum level, especially in those subjects affected from hyperphosphatemia. More specifically, the present invention relates to pharmaceutical compositions to be administered by oral route capable of absorbing phosphorus compounds from fluids of the enteric tract.

BACKGROUND OF THE INVENTION

Hyperphosphatemia is a pathologic condition due to different diseases, for example inadequate renal function, renal disease, kidney failure, in particular patients undergoing dialysis; hypoparatiroidism; osteoporosis, atherosclerosis. For a review of this problem, see U.S. Pat. No. 5,496,545 and references cited therein.

Cardiovascular alterations due to calcification of vessels, myocardium and heart valves represent the major mortality and morbidity cause in uremic patients (Burke, S. K., *Seminars in Nephrology*, vol. 24, no 5, 403-407, 2004; Levin, N V, et al.; *Seminars in Nephrology*, vol. 42, no 55, 396-400, 2004).

Most of patients undergoing dialysis or affected by chronic renal failure in conservative treatment show increased phosphorus serum levels, which are responsible of calcifications in tissues other than bone tissue and which are responsible of increased risk of cardiovascular mortality (Moe, S M, *Seminars in Nephrology*, vol. 24, no 5, 413-416, 2004; Eknoyan, G., et al.; *Am. Kidney Dis.*, 42, 4, 1-204, October 2003).

Phosphorus intake occurs with food and it is very difficult to avoid it. For example, patients undergoing dialysis must eat meat, a food rich in phosphorus. On the other hand, low-protein food has a low amount of phosphorus, but its use can determine malnutrition.

It was demonstrated by scientific evidence that prevention and/or early treatment of hyperphosphoremia in uremic patients can reduce morbidity and mortality risk. Moreover, increased phosphorus serum level can stimulate higher calcium deposition in cells and bone tissue protein and enzyme synthesis and increased risk of vessel calcification (Burke, ibid.).

Accordingly, controlling phosphorus serum levels is a necessary action for reducing cardiovascular morbidity and mortality in this kind of patients, but also can be a general health prevention in population, particularly exposed to risk of cardiovascular disease.

To date, high phosphorus serum levels are treated with vitamin D or substances, which, when administered by oral route, bind phosphorus through chelating action (phosphorus binders) and eliminate it by fecal route. Although effective in their action of eliminating phosphorus, some of these substances must be avoided because of their side effects, which, in some cases can be quite severe. For example, substances containing calcium, magnesium or aluminium are avoided by those expert in the field. Lanthanum is an effective absorbing substance but its toxicity is a hamper to its use in this field.

The current treatments are focused on absorbing phosphorus from food, the main source of it, by administering suitable drugs in concomitance with meals.

The leading therapy is represented by non-absorbed, calcium and metal-free phosphorus binders. A successfully marketed drug is Sevelamer (Renagel®), based on a polyallylamine, see U.S. Pat. No. 5,496,545, U.S. Pat. No. 5,667,775, U.S. Pat. No. 6,756,363 and U.S. Pat. No. 6,562,329.

Current therapy is used only to limit dietary phosphorus intake by binding phosphorus content in food, but is ineffective of phosphorus serum levels and cellular content.

The problem of an improved treatment of high phosphorus levels is still strongly felt by those skilled in the art, especially in view of the importance of such a treatment with respect to patients affected by renal diseases, in particular uremic patients undergoing dialysis.

The inventor discovered that, in the fasting interval, considerable amounts of phosphorus are secreted in saliva, which is continuously ingested and gastric secretions, so partly nullifying the therapeutic or preventive action of the drugs taken at the meals.

By this phenomenon, phosphorus is recirculated in the body and contributes to maintain high serum levels, thus making difficult to achieve an effective management of the risk of cardiovascular diseases, especially in those patients particularly exposed to said risk, such as patients affected by kidney failure and/or undergoing periodical dialysis.

SUMMARY OF THE INVENTION

The present invention is based on the discovery that saliva and other gastric secretions contain considerable amounts of phosphorus. In particular, saliva appears to be the main source of phosphorus, which is then recirculated in the body.

It has now been found that oral compositions of substances capable of binding phosphorus when administered during fasting periods achieve an improved treatment of hyperphosphatemia.

Due to the characteristics of the improved treatment, the oral compositions are characterized by a continuous slow release of the substances capable of binding phosphorus compounds.

Therefore, it is an object of the present invention a continuous slow release oral composition characterized by the prolonged, continuous slow release of a substance capable of binding phosphorus compounds.

The present invention comprises also an improved method for treating phosphate serum levels. In particular, the present invention provides a method for treating high phosphate serum levels by administering to a subject in need of such a treatment a continuous slow-release oral composition containing a substance capable of binding phosphorus compounds during fasting periods.

According to the present invention, a better control of phosphate serum levels is achieved, with immediate benefits to the patients and reduced risk of cardiovascular complications.

This and other objects and advantages of the present invention will be disclosed in detail also by means of examples.

DETAILED DESCRIPTION OF THE INVENTION

For the purposes of the present invention, oral composition is intended as any composition which can be administered by oral route to a subject.

Also for the purposes of the present invention, continuous slow release oral composition is intended a composition which releases in a continuous manner the active ingredient in the gastrointestinal tract, oral environment included. This feature does not only covers specially designed oral compositions for the continuous slow release of an active ingredient in the gastrointestinal tract, such as for example the so-called "cronoids", or sustained or delayed release type, but also any composition which, when retained in the mouth for a sufficient period of time, continuously releases in a slow manner the active ingredient.

Examples of oral composition are pills, lozenges, tablets, capsules, powdery compositions, solutions, suspensions, emulsions, preferably in the form of gel. According to the present invention, also some formulations pertaining to alimentary field are considered oral compositions, such as for example, confectionery, such as candies, gummy candies, chewing gum.

For the purposes of the present invention, as a substance capable of absorbing phosphorus compounds it is intended any substance for use as medicament which can bind phosphorus in a stable manner throughout the transit of the substance along the gastrointestinal tract until its elimination by fecal route. Examples of phosphorus binding are any kind of chemical bond, such as ionic bond, covalent bond, Van der Waals interactions, chelating phenomenon.

Examples of substances capable of absorbing phosphorus are phosphate binding polymers, such as those disclosed and mentioned in U.S. Pat. No. 5,496,545 and related patents. The currently marketed for of these phosphate binding polymers is a polyallylamine hydrochloride (Sevelamer-Renagel®), polyallylamine carbonate, and other pharmaceutically acceptable salts thereof, a pharmaceutically acceptable salt of lanthanum, for example carbonate, aluminium hydroxide, a pharmaceutically acceptable salt of magnesium, such as acetate, carbonate, a pharmaceutically acceptable salt of calcium, such as carbonate, acetate, citrate, alginate, and a pharmaceutically acceptable salt of a ketoacid, such as mentioned in the above U.S. Pat. No. 5,496,545; pharmaceutically acceptable anionic ion exchange resins, including those well-known with the trade mark Dowex® (styrene-divinylbenzene anion exchange resins), pharmaceutically acceptable phosphorus binding polysaccharides. Polyallylamine hydrochloride is a preferred embodiment of the present invention for the class of phosphate binding polymer. The most preferred embodiment of the present invention is chitosan for the class of phosphate binding polysaccharide.

In the most preferred embodiment of the present invention, chitosan is also used for the preparation of a medicament for the general treatment of hyperphosphatemia, including the administration of said medicament at meals, in order to absorb phosphorus compounds from food.

For the purposes of the present invention, as phosphorus compound is intended any substance containing phosphorus, for example phosphate, which, when absorbed in the body affects phosphatemia by increasing it.

In case of substances capable of absorbing phosphorus which can be absorbed in the gastrointestinal tract or their administration can imply side effects, the present invention is embodied in an oral composition characterized by the slow release of a substance capable of binding phosphorus and characterized in that said substance is substantially not absorbed in the gastrointestinal tract. Examples of this kind of sub-stances are aluminium hydroxide and/or magnesium hydroxide, calcium acetate, calcium carbonate.

For the purposes of the present invention, as substantially not absorbed in the gastrointestinal tract is intended that absorption is null or undetectable or does not increase serum phosphate level or does not involve side effects in the subject orally administered with said substance.

A first preferred embodiment of the present invention is an oral composition which can be retained for a long time in the mouth of the subject. Examples of such composition are a chewable tablet, a sachet, a mouthwash, a chewing gum, a gummy candy, a sucking tablet or candies. These compositions must be endowed with continuous slow release characteristics. Chewing gum is a more preferred embodiment, since it can be retained in the mouth for extended period, even hours.

This first embodiment of the present invention is advantageous since phosphate sequestration occurs in the mouth, in particular from saliva, the major source of recirculating phosphorus and once the composition has accomplished its scope, namely it has exhausted its absorbing capacity, can be directly taken out from the mouth and a new unit dose can be taken. This avoids swallowing the composition and engaging the gastrointestinal tract with the presence of a composition loaded with phosphorus, so that the subject has not to worry about a possible release of phosphorus in the gastrointestinal tract or the effective elimination of the composition.

A second preferred embodiment of the present invention is an oral composition which can be partly retained for a certain time in the mouth of the subject and subsequently swallowed. Examples of such composition is a chewable tablet, gummy candies, or candies. These compositions must be endowed with slow release characteristics.

This second embodiment of the present invention is advantageous since phosphorus sequestration, preferably in the form of phosphate, occurs in the mouth, in particular from saliva, the major source of recirculating phosphorus and once the composition has mostly accomplished its scope, namely it has exploited considerable part of its absorbing capacity, can be swallowed in order to continue its absorbing action through the gastrointestinal tract. This allows performing the intended treatment throughout the gastrointestinal tract with a single unit dose or a single administration of the composition.

This second embodiment can also be carried out by ingesting a composition according to the present invention and, after ingestion, taking a composition according to the first embodiment, retaining it in the mouth for a long time, until exhaustion of absorption capacity. The two unit doses, the first one to be immediately swallowed and the second one to be retained in the mouth until exhaustion of said binding agent for a therapeutic unit, can be conveniently packaged in a single therapeutic unit dose. The person skilled in the art can modify the therapeutic unit by varying the number and form of the unit doses, then providing a therapeutic unit with at least one first unit dose and at least one second unit dose.

A preferred example of composition to be ingested is a powdery composition, for example a sachet containing the composition in the form of a powder. Other forms of swallowable composition are well known in the art, for examples, capsules, pills, syrups, extemporary or ready-to-use solutions, suspensions, emulsions. The powdery composition may be soluble, partially soluble, insoluble or resulting in a suspension or emulsion in a suitable drinkable liquid.

An interesting combination of the first and second embodiment is a composition that can be retained in the mouth for a certain period in the form of mouthwash and subsequently swallowed.

The treatment according to the present invention is carried out during fasting period. Interestingly, the method according to the present invention can advantageously combined with the one of the state of the art, namely the administration at mealtimes of substances capable of absorbing phosphorus. In this way, a better control of phosphate serum level can be achieved.

In another preferred embodiment of the present invention, the composition, in particular those retained in the mouth, will be provided with detecting means signaling the complete absorption of phosphorus, namely the exhaustion of absorption capacity of the unit dose of the composition. In this way, the patient will be able to determine if and whether to discard the exhausted composition and to take another one according to medical advice.

A preferred embodiment of detecting means is a substance changing colour or becoming coloured in the presence of phosphorus. The person skilled in the art will find in the general common knowledge information about the above detecting means in order to carry out the present invention.

Alternatively, the composition according to the present invention can be supplied with separate detecting means, in order to check phosphorus level, for example in the form of phosphate, in saliva and to determine the duration of the treatment, namely how long to retain the composition in the mouth. A suitable example of such detecting means can be found in Tobey S L, Anslyn E V; *Org. Lett.*, 2003 Jun. 12; 5(12):2029-31.

It will be understood that the present invention is suitable for self-medication.

In the embodiment of the present invention wherein the phosphorus binder is Sevelamer, a preferred pharmaceutical composition is represented by slow-release tablets containing 250, 500 or 1,000 mg of Sevelamer. These tablets will bind about 46.75 mg, 93.50 mg and 187 mg of phosphorus, respectively, deriving from salivary and gastrointestinal secretion at pH about 7. The tablets are designed to be effective during diurnal and nocturnal fasting, but can be used also in different period of the day, according to medical prescription.

The dosage of the phosphorus-binding agent in the composition of the invention will be determined by the person skilled in the art according to standard dose finding tests. However, the dosage of the binding agent will preferably be in an amount sufficient to remove excess phosphorus with respect to physiological level. It would not be advisable to remove phosphorus in an amount such as to bring it at a level lower than physiological one, in order to avoid damage to teeth.

Slow-release tablets are within the general knowledge of the person skilled in the art and enabling disclosures are found in normal textbooks, such as for example Remington's Pharmaceutical Sciences, latest edition, Mack Publishing and Co.

A vast literature is available to the skilled person for the selection of the suitable formulation for the slow release of the active ingredient of interest, see for example U.S. Pat. No. 5,686,094 and references cited therein. U.S. Pat. No. 5,879,710 and references cited therein is an example of mucoadhesive pharmaceutical dosage form, suitable for the purposes of the present invention. U.S. Pat. No. 6,395,029 and references cited therein refer to slow release of polyanionic active ingredients, such as Sevelamer. Chewable soft gel is described in US 2004/0076664 and the references cited therein.

Normally, the tablet will contain at least one pharmaceutically acceptable vehicle and/or excipient. Examples of said vehicles and excipient are lactose anhydrous or monohydrate, povidone, microcrystalline cellulose, hydroxypropylcellulose, sodium croscaramellose, magnesium stearate, E, 171, E 172, mannitol, sodium laurylsulphate, ipromellose, methacrylic acid copolymer, macrogol, magnesium stearate, gelatine, saccharose, starch, sorbitol, mannitol, flavours, sodium saccharine, colloidal silica.

Tablets can be either chewed or swallowed, depending on where the desired effect of phosphorus absorption shall occur.

In the embodiment of the present invention wherein the phosphorus binder is Sevelamer, another preferred pharmaceutical composition is represented by capsules containing the same or different amount of Sevelamer. These capsules are designed to be effective in the same manner as the above-mentioned tablets, but mainly in the gastrointestinal tract, since they are taken and swallowed.

Slow-release capsules are within the general knowledge of the person skilled in the art and enabling disclosures are found in the same textbooks.

Normally, the capsule will contain at least one pharmaceutically acceptable vehicle and/or excipient and can be of the soft or rigid type. Examples of said vehicles and excipient are gelatine, titanium dioxide, sodium laurylsulphate.

Another embodiment of the present invention is represented by candies and gummy candies. These candies are designed to be effective mostly in the mouth, where the saliva is secreted.

Candies are within the general knowledge of the person skilled in the art and the field of confectionery industry can be considered a near technical field in this case.

Normally, the candies will contain the active ingredient and vehicles and/or excipients of use in confectionery (see for example *Food Industries Manual* (24th Edition) Edited by: Ranken, M. D.; Kill, R. C.; Baker, C. G. J. © 1997 Springer-Verlag). Examples of excipients are maltitol syrup, gum arabic, glycerol, aspartame, hydrogenated vegetal oil, gelatine, sorbitol, citric acid, pectin, caramel.

Sachets containing a soluble powder are another embodiment of the present invention and their preparation is within the normal task of a person of ordinary skill in the art.

Examples of vehicles and excipient are mannitol, sucrose, colloidal silica, methylcellulose, hydroxypropylcellulose. Excipient suitable to pre-pare a thick solution, suspension, emulsion, or preferably a gel are also well known in the art, see for example *Thickening and Gelling agents for Food*, second edition by Alan Imeson). A resulting gel formulation is more preferred in the embodiment of a mouthwash, which will be advantageous for patients with difficulty in chewing. Examples of gelling agents are 70% sorbitol.

It is within the general common knowledge that, for example tablets to be retained in the mouth until complete dissolution (for example suck-able tablets) will be prepared without disintegrating agents and will have high sugar content. Suitable non-disintegrating agent will be used, such as for example waxes, paraffin, fats.

Continuous slow-release compositions are intended for the purposes of the present invention any one of sustained release compositions, prolonged action compositions, repeat action compositions, otherwise generally named "cronoids" (E. Ragazzi *Lezioni di Tecnica Farmaceutica, Edizioni Libreria Cortina Padova*, 1982).

Slow release compositions are manufactured according to techniques which are part of the general common knowledge.

For example, differential release compositions can be prepared by means of granulates with differential coatings. The active ingredient (the binding agent according to the present invention) is mixed with a suitable excipient (for example lactose, starch) and transformed into a homogeneous granulate, which is subsequently coated with a suitable material (such as lac, shellac, zein, polyacrylic resins, waxes, fats, such as cacao butter, beeswax, stearic acid, etc.). The granules can then made up in a suitable pharmaceutical unit dose, such as capsules, tablet, multi-layered tablets. Alternatively, the active agent is adhered on an inert granulating support (sugar, starch, etc.) and transformed in a pill or a sugar-coated pill. Multi-layered tablets, in which a first layer will provide a "burst" of drug and a second or further layers will provide a continuous, slow release of drug, can be a convenient embodiment. Differential disintegration granules are also a suitable embodiment of the present invention, wherein the drug is incorporated in a lipophilic excipient (cacao butter, hydrogenated oils, glyceryl stearate, beeswax, carnauba wax, saturated fatty acids, etc.) and subsequently transformed into granules, which can optionally coated with different materials according to the desired release time and site.

"Erodible" layers are also a useful alternative.

The active agent can also be incorporated in a suitable polymeric matrix which will gradually and continuously release it. For example, ion exchange resins can be suitably selected depending on the pH of the desired site of release (mouth, stomach, gut).

One of the best modes for carrying out the invention is represented by chewing gum, since it allows to control the permanence of the phosphorus binder agent in the mouth at patience's will.

As per the case of candies, chewing gum preparation is within the normal exercise of a skilled person. Just for example, U.S. Pat. No. 3,818,807 and the references cited therein teaches a chewing gum with controlled flavour release composition; see also U.S. Pat. Nos. 4,386,106, 4,515,769 and references cited therein. EP 0 427 505 and the references cited therein offer an interesting embodiment for the present invention, since a low calorie chewing gum can be attractive for patients. IE 980990 and the references cited therein provide useful information for the manufacture of a medicated chewing gum with immediate release or sustained release or both. See also WO 02/074099 and the relevant art cited.

One possible formulation of a slow-release composition according to the present invention in the form of chewing gum comprises sorbitol, mannitol, 5% xylitol, maltitol syrup, aspartame, acesulfame k, gum base, glycerol, E320, polyalcohols, E903.

Another possible formulation of a slow-release composition according to the present invention comprises sorbitol, mannitol, 36% xylitol, maltitol syrup, sodium hydrogen carbonate, aspartame, acesulfame k, gum base, glycerol, E320, polyalcohols, E903.

In another best embodiment of the present invention, a method for the treatment of high phosphorus serum levels, or a method for controlling phosphorus serum levels in a subject in need thereof comprises the administration of a composition according to the present invention, said composition can be directly swallowed or chewed and swallowed, followed by taking a composition according to the present invention in the form of a chewing gum and retaining it in the mouth until complete exhaustion of binding capacity of the active ingredient. The chewing gum can incorporate phosphorus detecting means signalling the exhaustion of binding capacity or the chewing gum unit dose can be supplied with separate detecting means in order to periodically check phosphorus content in saliva.

All the above formulations can be adopted in the general frame of the present invention, thus meaning that they can be used with a generic phosphorus binding agent suitable for human use.

For those binding agent whose use could imply side effects, some measures will be adopted in order to avoid or minimize the side effects.

For example, if aluminium hydroxide or another aluminium derivative or lanthanum carbonate or another lanthanum derivative is the binding agent, for example in the form of tablets, the size of the particle comprising aluminium will be higher than 3 μm, in order to avoid intestinal absorption.

One exemplary tablet will comprise:

| | |
|---|---|
| Slow-release magnesium hydroxide | 250 mg |
| Slow-release aluminium hydroxide | 250 mg |

Sucrose powder, starch, sorbitol, mannitol, flavouring agents, sodium saccharinate, magnesium stearate.

If desired antiemetic or eukinetic agents can be added to or used in combination with the composition of the present invention.

The following examples further illustrate the present invention.

Example 1

Determination of Phosphorus in Saliva a) Uremic Patients Undergoing Dialytic Treatment 68 uremic patients (47 males and 21 females, aging 61.6±9.4) undergoing periodic bicarbonate dialysis (HD), three times weekly, using polysulphone dialyzer and 30 control healthy subjects of the same age were enrolled.

Uremic patients have been under dialytic treatment for at least one year, mean period 8.9±7.3 years. All patients were in good clinical conditions.

At the beginning of middle-week hemodialysis session, fasting patients and control subjects were subjected to blood withdrawal to dose serum phosphorus (P), calcium (Ca) and parathyroid hormone (PTH). A the same time, 2 ml of saliva samples were obtained, to dose phosphorus and calcium concentration.

Calcium and phosphorus were dosed by spectrophotometry using flex reagent cartridge by Dade Behring Inc., Newark, U.S.A. after centrifugation of the samples, while serum PTH was dosed by using Immulite 2000 intact PTH, solid phase, two site chemiluminescent enzyme labelled immunometric assay (Diagnostic Product Corporation, Los Angeles, U.S.A.).

Statistical analysis was performed as follows: salivary calcium and phosphorus, as well as the corresponding serum levels in HD patients were skewed, a logarithmic transformation was performed before analysis, and the results presented as geometric mean with 95% confidence intervals (CI). Regression analysis was used within HD patients to identify relevant relations between levels of salivary P and other parameters. To verify the association made by independent regression analysis when controlling other variables, multiple regression analysis was performed. Unpaired Student's t test was used to compare log transformed salivary P between controls and HD patients. Differences can be interpreted as the ratio of geometric means with 95% confidence intervals (CI). Upper limit of intervals for mean of salivary P was calculated in controls and a relationship for this value between controls and HD patients was established.

HD Patients Showed:
  serum Ca 8.73 mg/dl (geometric mean)—95% CI, 8.49 to 8.98, salivary Ca 7.21 mg/dl (geometric mean)—95% CI, 6.58 to 7.91;
  serum P 5.73±1.31 mg/dl (mean)—95% CI, 5.41 to 6.04; salivary P 30.27 mg/dl (geometric mean)—95% CI, 26.50 to 34.58.
  PTH 5.73±143.63 pg/ml (mean)—95% CI, 110.57 to 167.69. salivary P 30.27 mg/dl (geometric mean)—95% CI, 26.50 to 34.58.

Controls Showed:
salivary P 12.66±5.25 mg/dl (mean)—95% CI, 10.58 to 14.73.

Considering as cut off the upper limit of confidence intervals for mean of salivary P in controls (14.73 ml/dl), 62 out of 68 subjects had a value greater than cut off.

Salivary P was significantly correlated with serum P within HD patients (r=0.53, P<0.0001).

Considering that the quantity of daily salivary excretion ranges between 1,000 and 1,800 ml, it was calculated that salivary glands of the HD subjects were able to secrete a total amount of phosphate ranging from 302.7 to 544.86 ml.

b) Chronic Renal Failure Patients Under Conservative Treatment 110 patients (59 males and 51 females, aging 65; 17-90) under conservative treatment, were randomly selected at dialysis unit at Papardo Hospital in Messina, Italy. Care was taken to exclude patients on treatment with drugs known to interfere with phosphorus assay. Investigation protocol included serum creatinine and phosphorus assays as well as salivary phosphorus. After overnight fasting, blood (4 ml) and saliva (2 ml) samples were withdrawn, at 8.00 a.m. Glomerular filtration rate (GFR) was calculated according to MDRD equation [GFR (ml/min/1.73 m$^2$)=186×(Plasma creatinine)$^{-1.1154}$×(Age)$^{-0.203}$×(0.742 if female).

As salivary and serum phosphorus (P), age (yrs), GFR as well as serum creatinine values were skewed, data were log transformed before further parametric analysis was done. The results are presented as median and range. To assess possible relevant association between salivary P and demographic (age) and clinical characteristics, multiplicative regression analysis was used. To verify the associations made by univariate analysis when controlling for other variables, backward stepwise multiple regression analysis was performed. The results of the parsimonious model are shown. Differences between genders were tested by unpaired Student's t test.

TABLE 1

Clinical data in 110 subjects

| Parameter | Value |
|---|---|
| Creatinine (mg/dl) | 1.80 (0.50-7.60 |
| Serum Phosphorus | 3.76 (2.30-6.80) |
| Salivary Phoshorus | 31.20 (10.30-95.60 |
| GFR (ml/min/1.73 m$^{2*}$ | 35.77 (6.51-127.93 |

TABLE 2

Backward stepwise multiple regression model to predict salivary P: final model

| Variable | Coefficient b | Standard Error se | t | P |
|---|---|---|---|---|
| Constant | 2.133 | 0.356 | | |
| Creatinine (log$_e$ mg/dl) | 0.733 | 0.505 | 14.51 | <0.0001 |
| Age (log$_e$ yr) | 0.212 | 0.090 | 2.36 | 0.0204 |

Adjusted $R^2$ = 72.61 percent

Clinical data are shown in Table 1. A positive relationship (r=0.85, standard error=0.31, P<0.0001) was found between salivary P and creatinine with an index of determination ($R^2$) of 71.5 percent. At a lesser extent, the same was true for age (r=0.45, standard error=0.52, P<0.0001). A negative association was found for GFR (r=-0.85, standard error=0.32, P<0.0001). As expected, there was a positive relationship of creatinine with both age (r=0.39, standard error=0.32, $R^2$=15.4 percent, P<0.0001) and serum P (r=0.50, standard error 0.17, $R^2$=24.9 percent, P<0.0001). No relationship was found between serum P and age. A prevalence of male gender was found for salivary P (P=0.002), creatinina (P=0.08) and age (P=0.002). The backward stepwise multiple regression analysis selected only creatinine and age as independent predictor of salivary P (Table 2).

Example 2

Chitosan Formulation

Medium and low-viscosity chitosan sequestered phosphate quantity was determined by 500 MHz High-Resolution $^{31}$P-NMR (HR-NMR) with mono-dimensional spectra acquisition at 300° K.

The analysis was performed according two different protocols:

a) studying interaction of low- and medium-viscosity chitosan (FLUKA cat. 50494 and cat. 28191) and solution at different concentrations with PBS (Phosphate Buffered Saline—SIGMA), comparing the difference in phosphate amount between pure PBS and chitosan-containing PBS, in the same experimental conditions;

b) studying interaction of PBS with a medium-viscosity chitosan solution at different concentrations according to literature (Yong Zhang and M. Zhang, *J. Biomed. Mater. Res.*, 2002, Dec. 5, 5, 62(3):378-86).

Protocol a)

0.2, 1.0 and 1.5 g of low- and medium-viscosity chitosan were added to 10 ml of PBS to give 2, 10 and 15% p/v chitosan solutions.

Finally, solution was separated by centrifugation of residue sample.

0.5 ml solution were sampled for NMR analysis and added with 0.1 D$_2$O.

The results are shown in the following Table 1.

TABLE 1

| Concentration g/ml | | Medium | | Low | |
|---|---|---|---|---|---|
| (%) | PBS | PBS | Chitosan | PBS | Chitosan |
| 2 | 1 | 0.87 | 0.13 | 0.99 | 0.10 |
| 10 | 1 | 0.80 | 0.20 | 0.85 | 0.10 |
| 15 | 1 | 0.75 | 0.25 | 0.80 | 0.20 |

Protocol b)

1.0 and 2.0 g, respectively, of medium-viscosity chitosan were dissolved into 10 ml of 0.2 M acetic acid to give 10 and 20% p/v chitosan solutions. The obtained solutions were subsequently stirred at 50° C. for about 2 hours, in order to obtain a homogeneous polymer solution. The solution was filtered to remove air bubbles. The filtered solutions were added with 0.0931 g PBS and frozen at −20° C. to separate solids. Liquid phase was removed for NMR analysis.

0.5 ml test and reference (PBS) solutions were sampled for NMR analysis and added with 0.1 D$_2$O.

The results are shown in the following Table 2.

TABLE 1

| Concentration g/ml (%) | PBS | Medium | |
| --- | --- | --- | --- |
| | | Liquid phase | mixture |
| 10 | 1 | 0.70 | 0.30 |
| 20 | 1 | 0.80 | 0.40 |

Similar results were obtained with collagen and biocompatible polycationic polymers.

The invention claimed is:

1. A method of treating hyperphosphatemia in a subject in need thereof comprising:
    (a) orally administering during a fasting period, a chewing gum comprising an effective amount of a phosphorous binding agent selected from polyallylamine hydrochloride, polyallylamine carbonate, lanthanum carbonate, magnesium acetate, magnesium carbonate, calcium carbonate, calcium acetate, calcium citrate, calcium alginate, styrene-divinylbenzene anion exchange resins and chitosan, and at least one pharmaceutically acceptable vehicle and/or excipient, and
    (b) retaining the chewing gum in the mouth for a period of time sufficient for the phosphorous binding agent to sequester phosphorous compounds from the saliva of the subject and reduce salivary phosphorous levels thereby reducing recirculation of the phosphorous compounds in the body of the subject and reducing serum phosphorous levels, wherein the chewing gum is not swallowed.

2. The method according to claim 1, wherein said phosphorus binding agent is chitosan.

3. The method according to claim 1, wherein said treatment is for hyperphosphatemia in a disease selected from the group consisting of renal disease, kidney failure, hypoparathyroidism, osteoporosis and atherosclerosis.

4. The method according to claim 3, wherein said treatment is for hyperphosphatemia in uremic patients undergoing dialytic treatment.

5. The method according to claim 3, wherein said treatment is for hyperphosphatemia in chronic renal failure patients under conservative treatment.

6. A method of treating hyperphosphatemia in a subject in need thereof comprising:
    (a) ingesting at mealtime one or more phosphorous binding agents;
    (b) orally administering during a fasting period, a chewing gum comprising an effective amount of a phosphorous binding agent selected from polyallylamine hydrochloride, polyallylamine carbonate, lanthanum carbonate, magnesium acetate, magnesium carbonate, calcium carbonate, calcium acetate, calcium citrate, calcium alginate, styrene-divinylbenzene anion exchange resins and chitosan, and at least one pharmaceutically acceptable vehicle and/or excipient;
    (c) retaining the chewing gum in the mouth for a period of time sufficient for the phosphorous binding agent to sequester phosphorous compounds from the saliva of the subject and reduce salivary phosphorous levels, thereby reducing recirculation of the phosphorous compounds in the body of the subject and reducing serum phosphorous levels; and
    (d) removing the chewing gum from the mouth of the subject.

7. The method of claim 6, wherein the phosphorous binding agent is chitosan.

8. The method of claim 6, wherein the substance capable of absorbing phosphorous is sevelamer.

9. The method of claim 6, wherein the subject is a uremic patient undergoing dialytic treatment.

10. A method of treating hyperphosphatemia in a subject in need thereof comprising:
    (a) administering at mealtime sevelamer;
    (b) orally administering, during a fasting period, a chewing gum comprising an effective amount of chitosan and at least one pharmaceutically acceptable vehicle and/or excipient, and
    (c) retaining the chewing gum in the mouth for a period of time sufficient for the chitosan to sequester phosphorous compounds from the saliva of the subject and reduce salivary phosphorous levels thereby reducing recirculation of the phosphorous compounds in the body of the subject and reducing serum phosphorous levels, wherein the chewing gum is not swallowed.

11. A method of treating hyperphosphatemia in a subject in need thereof comprising:
    (a) orally administering during a fasting period, a chewing gum comprising an effective amount of chitosan, and at least one pharmaceutically acceptable vehicle and/or excipient;
    (b) retaining the chewing gum in the mouth for a sufficient time to reduce the salivary phosphorous level of the subject by at least 15%; and
    (c) removing the chewing gum from the mouth of the subject.

* * * * *